(12) United States Patent
Omi (10) Patent No.: US 9,892,333 B2
(45) Date of Patent: Feb. 13, 2018

(54) VIEWING AREA ESTIMATION DEVICE (71) Applicant: DENSO CORPORATION, Kariya, Aichi-pref. (JP)

(72) Inventor: Takuhiro Omi, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 69 days.

(21) Appl. No.: 15/039,015

(22) PCT Filed: Nov. 19, 2014

(86) PCT No.: PCT/JP2014/005819
§ 371 (c)(1),
(2) Date: May 24, 2016

(87) PCT Pub. No.: WO2015/079657
PCT Pub. Date: Jun. 4, 2015

(65) Prior Publication Data
US 2017/0169302 A1    Jun. 15, 2017

(30) Foreign Application Priority Data

Nov. 27, 2013  (JP) ................................. 2013-245088

(51) Int. Cl.
G06K 9/00    (2006.01)
G06K 9/03    (2006.01)

(52) U.S. Cl.
CPC ..... G06K 9/00845 (2013.01); G06K 9/00255 (2013.01); G06K 9/00261 (2013.01); G06K 9/00281 (2013.01); G06K 9/03 (2013.01)

(58) Field of Classification Search
CPC . B60W 2040/0818; B60W 2040/0863; B60W 40/09; B60W 2540/30;
(Continued)

(56) References Cited

U.S. PATENT DOCUMENTS

2005/0073136 A1*  4/2005  Larsson ................ A61B 3/113
                                                    280/735
2009/0268025 A1   10/2009  Hiramaki et al.
2010/0049375 A1*  2/2010  Tanimoto .............. B60T 7/12
                                                    701/1

FOREIGN PATENT DOCUMENTS

JP    H06-270712 A    9/1994
JP    H09-238905 A    9/1997
(Continued)

Primary Examiner — Stephen R Koziol
Assistant Examiner — Raphael Schwartz
(74) Attorney, Agent, or Firm — Knobbe, Martens, Olson & Bear, LLP (57) ABSTRACT

A viewing area estimation device, which estimates a viewing area visually confirmed by a monitored subject, includes a captured image acquisition portion acquiring a plurality of chronologically captured images of a face of a monitored subject, a face direction detection portion detecting, based on the plurality of captured images, a face direction of the monitored subject and a stationary period representing a duration in which a face direction change of the monitored subject is in a stop state or in an almost stop state, and a direction estimation portion estimating the viewing area based on parameters including the face direction of the monitored subject and the stationary period of the face direction change.

7 Claims, 5 Drawing Sheets

(58) Field of Classification Search
CPC .......... B60W 2540/20; G06K 9/00845; G06K 9/00597–9/00617; B60R 21/01552
See application file for complete search history.

(56) References Cited

FOREIGN PATENT DOCUMENTS

| | | |
|---|---|---|
| JP | 3785669 B2 | 6/2006 |
| JP | 2008-225578 | 9/2008 |
| JP | 2009-120148 | 6/2009 |
| JP | 2009-120148 A | 6/2009 |

* cited by examiner

- FACE DIRECTION (YAW/PITCH/ROLL)
- FACE POSITION (HORIZONTAL/VERTICAL/DEPTH)

VIEWING AREA ESTIMATION DEVICE

CROSS REFERENCE TO RELATED APPLICATION

This application is based on Japanese Patent Application No. 2013-245088 filed on Nov. 27, 2013, the present disclosure of which is incorporated herein by reference.

TECHNICAL FIELD

The present disclosure relates to a viewing area estimation device which estimates a viewing area of a monitored subject.

BACKGROUND ART

As the above-described viewing area estimation device, a publicly known viewing area estimation device estimates a viewing area viewed by a monitored subject by detecting positions of the eyeballs of the monitored subject using a camera (see patent literature 1).

However, the viewing area estimation device may not be able to detect an eyeball position when an image capturing condition is affected by a light source, such as sunlight or an illumination or an accessory, such as eyeglasses worn by the monitored subject. In such a case, estimation of a viewing area becomes difficult.

PRIOR ART LITERATURES

Patent Literature

[Patent Literature 1] Japanese Patent No. 3785669

SUMMARY OF INVENTION

In view of the foregoing difficulties, it is an object of the present disclosure to provide a viewing area estimation device which estimates a viewing area of a monitored subject and is capable of more properly estimating a viewing area of the monitored subject regardless of image capturing conditions.

According to an aspect of the present disclosure, a viewing area estimation device, which estimates a viewing area visually confirmed by a monitored subject, includes a captured image acquisition portion, a face direction detection, and a direction estimation portion. The captured image acquisition portion acquires multiple chronologically captured images of a face of a monitored subject. The face direction detection portion detects, based on the captured images, a face direction of the monitored subject and a stationary period representing a duration in which a face direction change of the monitored subject is in a stop state or in an almost stop state. The direction estimation portion estimates the viewing area based on parameters including the face direction of the monitored subject and the stationary period of the face direction change.

In the above viewing area estimation device, a viewing area is estimated based on the face direction and a stationary period of the face direction, both of which are more easily recognized than the eyeball position of the monitored subject. Thus, the viewing area estimation device can more reliably estimate a viewing area even when an eyeball position of the monitored subject cannot be recognized.

BRIEF DESCRIPTION OF DRAWINGS

The above and other objects, features and advantages of the present invention will become more apparent from the following detailed description made with reference to the accompanying drawings. In the drawings.

EMBODIMENTS FOR CARRYING OUT INVENTION

The following will describe embodiments of the present disclosure with reference to the accompanying drawings.

Configuration of the Embodiment

The viewing area estimation device according to the present disclosure is applied to a safety confirmation alarm device 1 equipped to a vehicle, such as an automobile. The safety confirmation alarm device 1 monitors whether or not a vehicle driver visually checks an area needed for safety confirmation such as mirrors or the right and the left sides at an intersection. The safety confirmation alarm device 1 has a function that recognizes the driver's failure to visually check the confirmation-needed area, calls the driver's attention, and prompts the driver to perform the safety confirmation.

Figure 1:
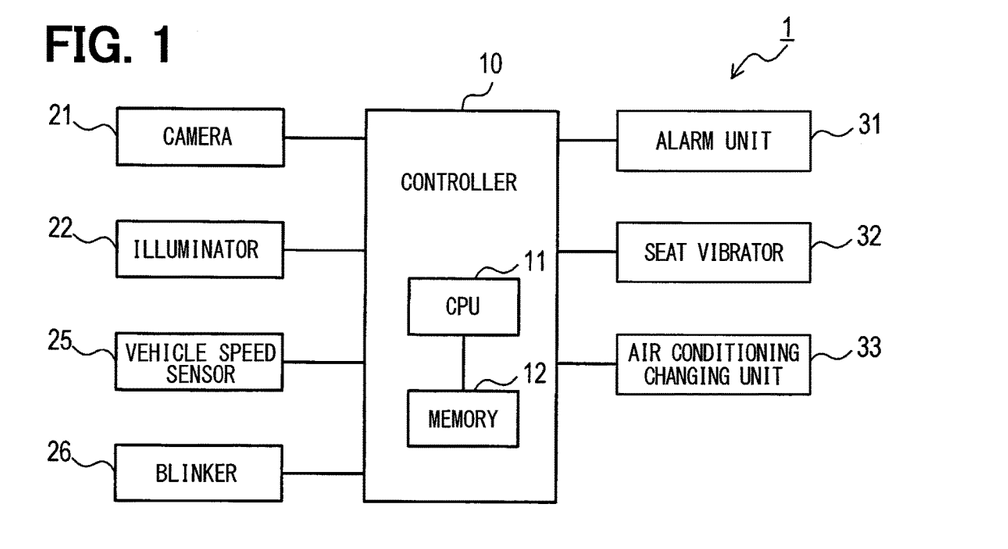
FIG. 1 is a block diagram illustrating a schematic configuration of a safety confirmation alarm device to which the present disclosure is applied.

As illustrated in FIG. 1, the safety confirmation alarm device 1 includes a controller 10, a camera 21, an illuminator 22, a vehicle speed sensor 25, a blinker 26, an alarm unit 31, a seat vibrator 32, and an air conditioning changing unit 33.

The camera 21 is placed ahead of the driver seat in the vehicle, and an image capture range of the camera 21 is set to include the driver's face.

The illuminator 22 functions as an auxiliary light source for the camera 21, and irradiates infrared rays to the driver's face. The illuminator 22 may be in always-on state to irradiate infrared rays steadily. Alternatively, the controller 10 may control the operation time of infrared ray irradiation to synchronize with an image capture cycle of the camera 21.

The vehicle speed sensor 25 is configured as a publicly known vehicle speed sensor and detects a speed of the vehicle to which the safety confirmation alarm device 1 is equipped. A vehicle speed detected by the vehicle speed sensor 25 is configured so that the controller 10 recognizes the vehicle speed.

The blinker 26 is configured as a publicly known directional signal lamp, and multiple blinkers 26 are provided at right and left portions of the vehicle. An operation state of the blinker 26 is configured so that the controller 10 recognizes the operation state.

The alarm unit 31 receives an instruction from the controller 10, and audibly or visually calls the driver's attention for alert purpose.

The seat vibrator 32 is configured as a vibrator embedded in the driver's seat and operates based on an instruction transmitted from the controller 10.

The air conditioning changing unit 33 receives an instruction from the controller 10 to change an air volume, wind direction, or preset temperature of an air conditioner equipped to the vehicle.

The controller 10 is configured as a publicly known computer including a CPU 11 and a memory 12 such ROM and RAM. The CPU 11 performs various processes (to be described later) according to a program stored in the memory 12.

Processes of the Embodiment

Figure 2:
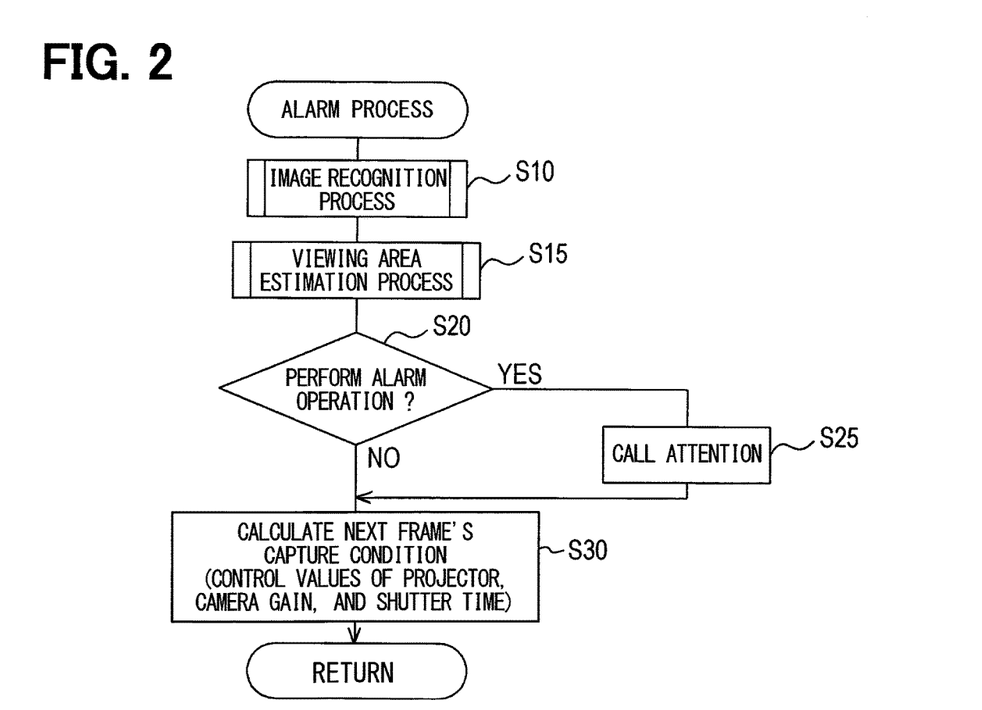
FIG. 2 is a flowchart illustrating an alarm process executed by a controller (CPU) according to an embodiment of the present disclosure.

The controller 10 in the safety confirmation alarm device 1 having the above-described configuration performs an alarm process in FIG. 2. The alarm process estimates a viewing area, namely, a specified angular range with reference to a direction of a visual line. The alarm process determines whether or not the driver visually checks an area needed for safety confirmation in a case where the safety confirmation is required. The alarm process calls the driver's attention when the driver does not visually check the area. When the safety confirmation alarm device 1 is powered on, the controller 10 starts the alarm process.

Figure 3:
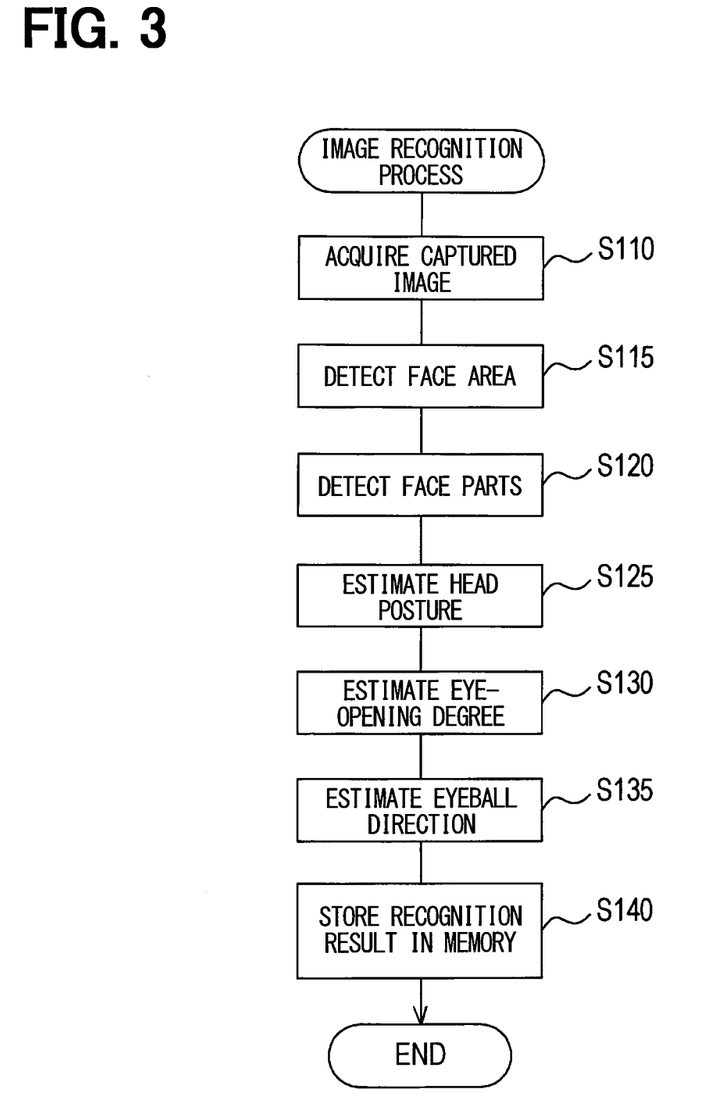
FIG. 3 is a flowchart illustrating an image recognition process included in the alarm process.

The controller 10 performs an image recognition process (S10) as illustrated in FIG. 2. The image recognition process recognizes a driver state based on an image captured by the camera 21. The image recognition process acquires a captured image from the camera 21 (S110) as illustrated in FIG. 3.

Figure 4A:
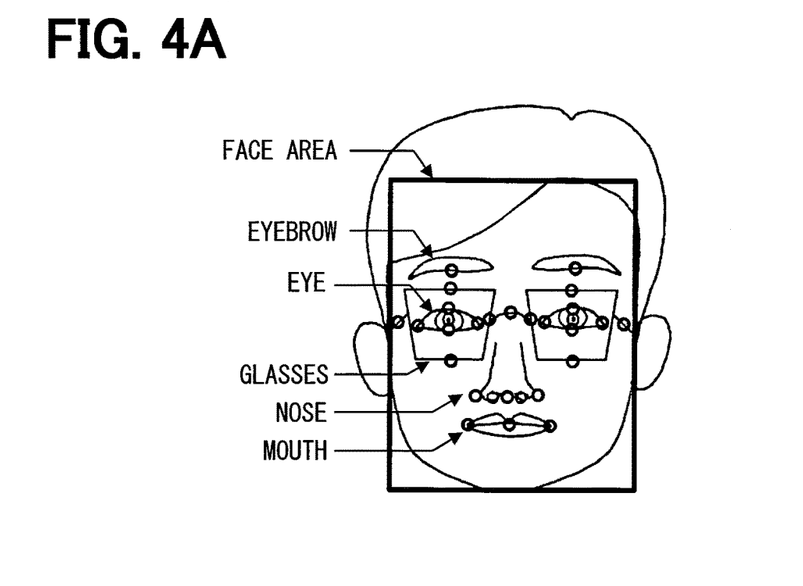
FIG. 4A is an explanatory diagram illustrating how to recognize face parts of the monitored subject.

The controller 10 extracts a face area from the captured image (S115) and then extracts face parts (S120). As illustrated in FIG. 4A, the controller 10 performs the processes to process the captured image, recognize an area similar to the face shape, and recognize a rectangular area containing the area similar to the face shape as a face area. The controller 10 detects an edge in the face area and specifies a face part by recognizing a shape of the face part. The edge is a portion at which brightness is different from the adjacent pixels and the brightness difference is higher than or equal to a predetermined reference value. The embodiment is not limited to the above-described method for specifying the face parts, and may use a different publicly known method.

Figure 4B:
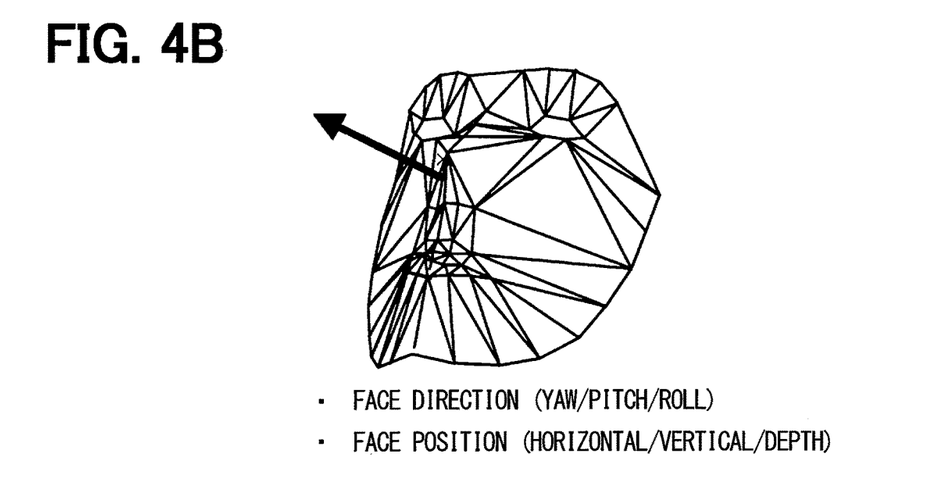
FIG. 4B is an explanatory diagram illustrating how to recognize a face direction of the monitored subject.

Next, the controller 10 estimates a head posture (S125). This process estimates a face direction as illustrated in FIG. 4B based on positional relationship between face parts. The controller 10 species a face direction angle with reference to a reference direction such as a vehicle travel direction or a direction toward the front of the vehicle.

When estimating a head posture, the controller 10 uses information about head postures estimated in the past to calculate an angular velocity of a face direction change and a stationary period during which the face direction change completely or almost in stop state. Almost stopping state of a face direction change indicates a state in which an angular velocity toward the changing direction of the face direction is smaller than or equal to a predetermined threshold value that can be assumed to indicate an almost stop state. For example, a state in which the most recent angular acceleration has a negative value and the angular velocity is 0.1 rad/s or less may be assumed as the almost stop state.

The controller 10 then estimates an eye-opening degree (S130). In this process, the controller 10 specifies a curvature radius for an eyelid curve (an upper edge of the eyeball) using the eye as a face part. When the curvature radius increases, the eye-opening degree is assumed to be decreased.

The controller 10 estimates an eyeball direction with reference to the face when the eye-opening degree is greater than or equal to a threshold value (S135). The eye-opening degree threshold value specifies an eye-opening degree that enables recognition of an eyeball (iris position). The eye-opening degree threshold value may be set to approximately 25%. The visual line direction can be estimated based on the face direction and the eyeball position with reference to positions corresponding to both corners of the eye.

The controller 10 uses the memory to store estimation results of the face direction angle, the angular velocity of the face direction change, the stationary period, and the eyeball direction with reference to the face (S140). When the extraction of the eyeball direction is failed or the recognition result has a low likelihood (credibility), the controller 10 may store information indicating these situations in the memory 12. Further, the information indicating failure to extract the eyeball direction may be managed by setting a flag.

When completing these processes, the controller 10 terminates the image recognition process. When the image recognition process terminates, the controller 10 performs a viewing area estimation process (S15) in FIG. 2. The viewing area estimation process estimates a viewing area of the driver.

Figure 5:
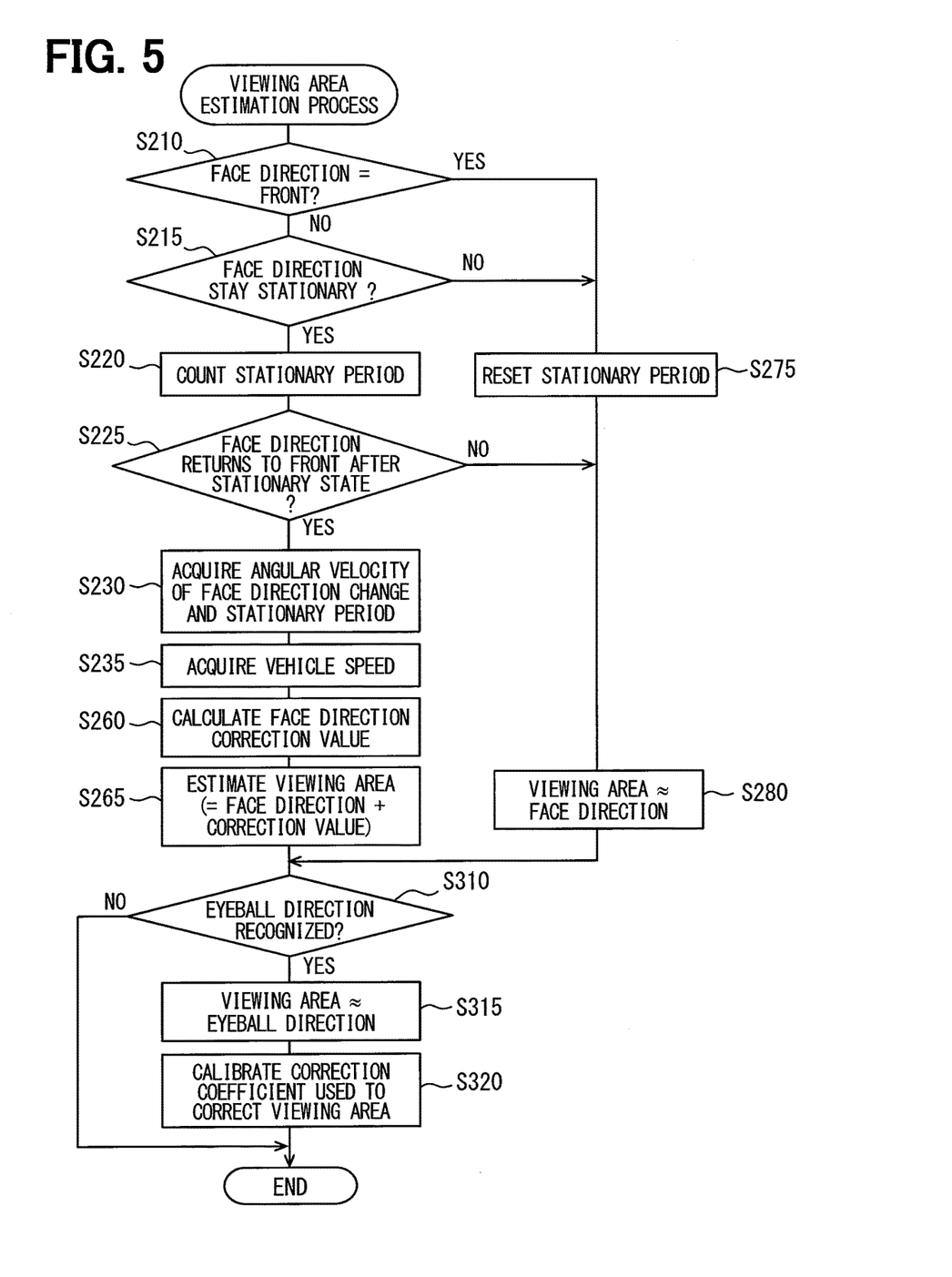
FIG. 5 is a flowchart illustrating a viewing area estimation process included in the alarm process.

The controller 10 performs the viewing area estimation process to determine whether or not the face of the driver is approximately directed toward the front of the vehicle (S210) as illustrated in FIG. 5. To determine whether or not the face of the driver is approximately directed toward the front of the vehicle, the controller 10 determines whether or not the face direction follows the reference direction within an allowance represented by a threshold value (approximately 10 degrees).

When the driver's face direction approximately corresponds to the front (S210: YES), the controller 10 proceeds to the process at S280 to be described later. When the driver's face direction does not approximately correspond to the front (S210: NO), the controller 10 determines whether the face direction is retained in the most recent process or in the current process (S215).

When both conditions are not satisfied (S215: NO), the controller 10 stops counting of the stationary period and resets the stationary period (S280). The stationary period represents a duration during which the face direction change is in the stop state. The controller 10 sets the position corresponding to the face direction as a viewing position of the driver, and sets a surrounding area (within a range of three degrees or less) around the viewing position as a viewing area (S280). When completing this process, the controller 10 proceeds to S310 to be described later.

In the process at S215, when one of the conditions is satisfied (S215: YES), the controller 10 starts or continues counting the stationary period (S220). Then, the controller 10 determines whether or not the face direction moves toward the front (reference direction) after the stationary state (S225).

When the face direction does not move toward the front (S225: NO), the controller 10 proceeds to S280. When the face direction moves toward the front (S225: YES), the controller 10 acquires the angular velocity in the face direction and the stationary period (S230). The controller 10 acquires a vehicle speed (S235), and the controller 10 calculates a face direction correction value (S260).

The following mathematical function may be used to calculate the face direction correction value.

Correction value=$f(k1\times$(face direction angular velocity level)+$k2\times$(face direction stationary period)+$k3\times$(face direction angle zone)+$k4\times$(vehicle speed)+$k5\times$(trip duration)+$k6\times$(fatigue level)) [Expression 1]

Each term is characterized as follows.

Face direction angular velocity level: Correction value increases with an increasing of the face direction angular velocity.

Face direction stationary period: Correction value increases with a decrease of the stationary period.

Face direction angle zone: Correction value increases with an increase of the deviation angle from the front direction.

Vehicle speed: Correction value has a small value when the vehicle speed is equal to zero, and the correction value increases with an increase of the vehicle speed.

Trip duration: Correction value increases with an increase of the trip duration.

Fatigue level: Correction value increases with an increase of the fatigue level.

The fatigue level can be specified based on an eye-opening degree or the number of blinks (blinking cycle). In the above-mentioned function, coefficients k1 through k6 are weighted by a value found from experimental results. In principle, the coefficients are set to positive values. However, the coefficients may be set to negative values depending on situations.

Figure 6:
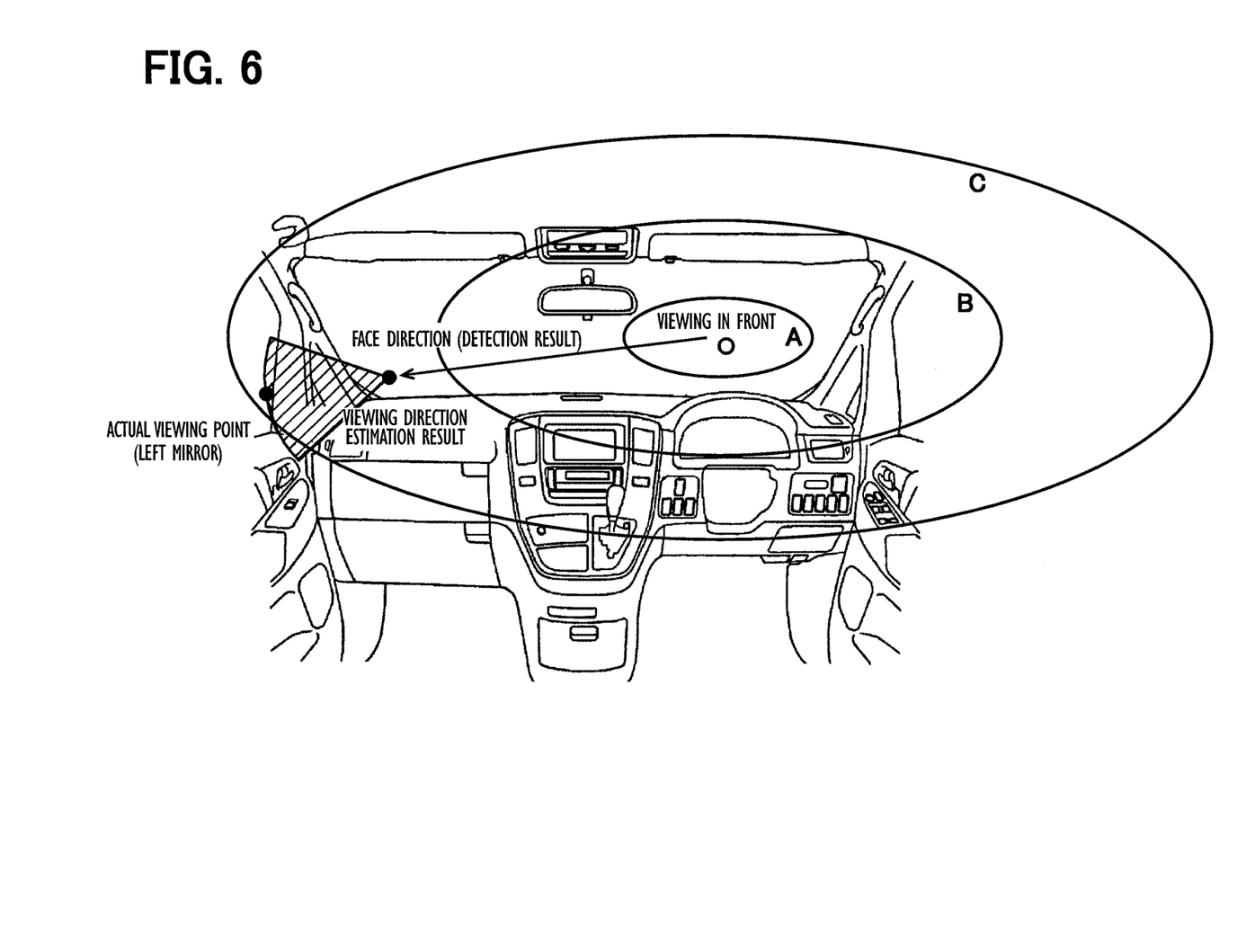
FIG. 6 is an explanatory diagram illustrating a concept of a viewing area.

Here, the correction value represents the direction spreading in a fan-like form from the direction specified by the face direction as illustrated in FIG. 6. An increase of the correction value widens a fan-shaped area.

The controller 10 then estimates a viewing area (S265). As illustrated in FIG. 6, in this process, the controller 10 sets, as a viewing position, the position (fan-shaped area) corresponding to a new direction obtained by adding the correction value of the face direction to the specified face direction. The controller 10 estimates an area containing the viewing position to be the viewing area (extending up to three degrees each from the viewing position).

The controller 10 then refers to the memory 12 to determine whether or not the eyeball direction is recognized (S310). When the eyeball direction is not recognized (S310: NO), the controller 10 terminates the viewing area estimation process.

When the eyeball direction is recognized (S310: YES), the controller 10 sets the area containing the eyeball direction as a viewing area (S315). The controller 10 then calibrates a correction coefficient used to correct the viewing area (S320).

This process sets, as a correct viewing area, the area corresponding to the eyeball direction (the area around the eyeball direction). The process is used to change a computation method for calculating the correction value so that a viewing area obtained based on the face direction conforms to a viewing area obtained based on the eyeball direction. For example, the process resets the coefficients (k1 through k6) used to calculate the correction value. The reset of the coefficients is preferably performed by averaging weights using past values or providing a hysteresis so that the correction value is prevented from being changed sensitively.

When the viewing area estimation process terminates, returning to FIG. 2, the controller 10 determines whether or not to provide an alarm (S20). Here, for example, when the blinker 26 is in blinking operation state, the controller 10 monitors whether or not an area containing a right or left mirror matches with the viewing area of the driver. The controller 10 determines to activate an alarm when both areas do not match with the viewing area of the driver. The controller 10 determines not to activate the alarm when at least one of the two areas matches with the viewing area of the driver at least once after the blinker 26 starts operation.

For example, the controller 10 may acquire information about entry into an intersection from a publicly known navigation system. After receiving this information, the controller 10 may provide an alarm depending on whether or not the driver has confirmed right or left. For example, after receiving the information about entry into an intersection, the controller 10 may determine whether or not the viewing area matches with an area containing the right or left window within a specified time period. The controller 10 may determine to activate an alarm when no match is found. After receiving the information about entry into an intersection, the controller 10 may determine not to activate an alarm when the viewing area matches with an area containing the right or left window at least once.

When determining not to activate an alarm (S20: NO), the controller 10 proceeds to the process at S30 to be described later. When determining to activate an alarm (S20: YES), the controller 10 calls the driver's attention using any one of hardware devices such as the alarm unit 31, the seat vibrator 32, or the air conditioning changing unit 33 (S25).

The process may change alarm types or a combination of hardware used for alarm according to the time to continue an alarm or the number of alarm occurrences.

The controller 10 calculates conditions (a projector and control values including the camera gain and the shutter time) to capture an image for the next frame in order to acquire a favorably captured image to be used in the next recognition (S30). The controller 10 then returns to the process at S10. Specifically, the controller 10 feeds back images in the past to change an exposing condition so that a skin part of the face to be captured satisfies a specified pixel value (brightness).

Effects of the Embodiment

The controller 10 in the safety confirmation alarm device 1 chronologically acquires multiple captured images of the face of the monitored subject. Based on the captured images, the controller 10 detects the face direction of the monitored subject and the stationary period during which the face direction of the monitored subject is completely or almost in stop state. The controller 10 estimates a viewing area based on parameters including the face direction of the monitored subject and the stationary period of the face direction.

The safety confirmation alarm device 1 estimates a viewing area based on the face direction and the stationary period of the face direction that can be more easily recognized than the eyeball position of the monitored subject. Thus, the safety confirmation alarm device 1 can more properly estimate a viewing area even when the eyeball position cannot be recognized due to an influence of ambient light or the like.

The controller 10 in the safety confirmation alarm device 1 determines a direction corresponding to the face of the monitored subject orientation as a temporary direction. The controller 10 sets a correction value for correcting the temporary direction based on parameters including the stationary period. The controller 10 corrects the temporary direction so that the face direction of the monitored subject deviates from a predetermined reference direction by a greater amount with an increase of the correction value allows. The controller 10 sets an area corresponding to the corrected temporary direction as a viewing area of the monitored subject.

Such a safety confirmation alarm device 1 sets a temporary direction according to the face direction of the driver, and corrects the temporary direction to specify a viewing area. Thus, the safety confirmation alarm device 1 can fine-tune the viewing area position simply by changing the correction value. Accordingly, the safety confirmation alarm device 1 can simplify the process for estimating a viewing area.

The controller 10 in the safety confirmation alarm device 1 increases the correction value with a decrease of the stationary period. Usually, when the stationary period is short, an average person tends to move only the visual line after stopping the face direction. The viewing area estimation uses this tendency.

The controller 10 in the safety confirmation alarm device 1 increases the correction value when a face direction in completely or almost stop state of the face movement of the monitored subject deviates from the reference direction by a greater amount.

Usually, a moving range of the visual line of an average person increases with an increase of the face direction movement range. The viewing area estimation uses this tendency of average person.

The controller 10 in the safety confirmation alarm device 1 acquires a rotational angular velocity of the face direction of the monitored subject. The controller 10 increases the correction value with an increase of the rotational angular velocity of the face direction until the face direction of the monitored subject becomes to completely or almost stop state.

Usually, the visual line movement of an average person tends to increase with an increase of the rotational angular velocity of the face direction. The viewing area estimation uses this tendency of average person.

In addition, the controller 10 in the safety confirmation alarm device 1 acquires a travel speed of the vehicle. When the monitored subject completely or almost stops the face direction, the controller 10 increases the correction value with an increase of the travel speed.

Usually, as the travel speed increases, a driver tends to move only the visual line for safety confirmation by minimizing a change in the face direction from the vehicle travel direction. The viewing area estimation uses this tendency.

The above-described safety confirmation alarm device 1 can accurately estimate a viewing area because the estimation is carried out based on tendencies of human action.

Moreover, the controller 10 in the safety confirmation alarm device 1 detects the position of the eyeball of the monitored subject based on a captured image. The controller 10 estimates a viewing area according to the eyeball position. Using this viewing area, the controller 10 corrects a setup value used to estimate a viewing area acquired from the face direction and the stationary period. The controller 10 also corrects the estimated viewing area based on already known vehicle information or locations frequently and visually checked by a driver such as a mirror, a meter, a navigation system, and an audio instrument.

Here, the setup value may adopt the before-mentioned correction value (including coefficients to specify the correction value) or a correction amount of the before-mentioned parameter. Such a safety confirmation alarm device 1 can calibrate relationship among the face direction, the stationary period, and the viewing area when the eyeball position is recognized. Accordingly, the safety confirmation alarm device 1 can improve the accuracy of estimating a viewing area when the eyeball position cannot be recognized.

When the eyeball position can be estimated, the controller 10 in the above safety confirmation alarm device 1 sets the viewing area estimated according to the eyeball position as a final viewing area. When the eyeball position cannot be estimated, the controller 10 sets the viewing area estimated based on the face direction and the stationary period as a final viewing area.

Such a safety confirmation alarm device 1 can estimate a viewing area using a technique assumed to be highly accurate depending on situations.

It is noted that a flowchart or the processing of the flowchart in the present disclosure includes sections (also referred to as steps), each of which is represented, for instance, as S10. Further, each section can be divided into several sub-sections while several sections can be combined into a single section. Furthermore, each of thus configured sections can be also referred to as a circuit, device, module, or means.

Each or any combination of sections explained in the above can be achieved as (i) a software section in combination with a hardware unit (e.g., computer) or (ii) a hardware section, including or not including a function of a related apparatus; furthermore, the hardware section (e.g., integrated circuit, hard-wired logic circuit) may be constructed inside of a microcomputer.

Other Embodiments

According to the above embodiment, the controller 10 monitors an angular velocity when the face direction varies to deviate from the reference direction. Alternatively, the controller 10 may monitor an angular velocity when the face direction returns from a deviated position to the reference direction. In this case, the technique to specify a correction value for the face direction may consider an angular velocity of the face direction returning from the deviated position to the reference direction.

In addition, suppose that the technique to specify a correction value for the face direction takes into account an angular velocity to return to the reference direction. In this case, the computation may use different functions (terms) depending on whether the face direction varies to deviate from the reference direction or the face direction varies to returns to the reference direction.

The controller 10 according to the embodiment corresponds to a viewing area estimation device in the present disclosure. Among the processes executed by the controller 10 according to the embodiment, the process executed at S15 corresponds to a direction estimation portion in the present disclosure.

The process executed at S110 according to the embodiment corresponds to a captured image acquisition portion in the present disclosure. The process executed at S125 according to the embodiment corresponds to a face direction detection portion and an angular velocity acquisition portion in the present disclosure. The process executed at S125 and S135 according to the embodiment corresponds to an eyeball estimation portion in the present disclosure. The process executed at S230 according to the embodiment corresponds to a temporary direction setup portion in the present disclosure.

The process executed at S235 according to the embodiment corresponds to a travel speed acquisition portion in the present disclosure. The process executed at S260 according to the embodiment corresponds to a correction value setup portion in the present disclosure. The process executed at S265 according to the embodiment corresponds to an area setup portion in the present disclosure. The process executed at S310 and S315 according to the embodiment corresponds to a selection portion in the present disclosure.

The process executed at S320 according to the embodiment corresponds to an estimation correction portion in the present disclosure.

To achieve the object, the present disclosure may be applied to a viewing area estimation program which is computer readable and controls a computer to function as the above-described portions configuring the viewing area estimation device described above.

While the present disclosure has been described with reference to preferred embodiments thereof, it is to be understood that the present disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

The invention claimed is:

1. A viewing area estimation device, which estimates a viewing area visually confirmed by a monitored subject, comprising:
a captured image acquisition portion acquiring a plurality of chronologically captured images of a face of a monitored subject;
a face direction detection portion detecting, based on the plurality of captured images, a face direction of the monitored subject and a stationary period representing a duration in which a face direction change of the monitored subject is in a stop state or in an almost stop state; and
a direction estimation portion estimating the viewing area based on parameters including the face direction of the monitored subject and the stationary period of the face direction change
wherein the direction estimation portion includes:
a temporary direction setup portion setting a direction corresponding to the face direction of the monitored subject as a temporary direction;
a correction value setup portion setting, based on the parameters including the stationary period, a correction value to be used for correcting the temporary direction;
and an area setup portion correcting the temporary direction so that the temporary direction, which indicates the face direction of the monitored subject, deviates from a predetermined reference direction by a greater amount in accordance with an increase of the correction value, and the area setup portion setting an area corresponding to the temporary direction that is corrected as the viewing area.

2. The viewing area estimation device according to claim 1, wherein
the correction value setup portion increases the correction value with a decrease of the stationary period of the face direction change.

3. The viewing area estimation device according to claim 1, wherein
the correction value setup portion increases the correction value when the face direction of the monitored subject is deviated from the predetermined reference direction by a greater amount under a condition that the face direction change of the monitored subject is in the stop state or in the almost stop state.

4. The viewing area estimation device according to claim 1, to further comprising:
an angular velocity acquisition portion acquiring a rotational angular velocity of the face direction change of the monitored subject,
wherein the correction value setup portion increases the correction value with an increase of the rotational angular velocity of the face direction change of the monitored subject until the face direction change of the monitored subject enters the stop state or the almost stop state.

5. The viewing area estimation device according to claim 1, wherein
the viewing area estimation device is equipped to a vehicle and a driver of the vehicle is set as the monitored subject,
the viewing area estimation device further comprises a travel speed acquisition portion acquiring a travel speed of the vehicle, and
the correction value setup portion increases the correction value with an increase of the travel speed of the vehicle under a condition that the face direction change of the monitored subject is in the stop state or in the almost stop state.

6. The viewing area estimation device according to claim 1, further comprising:
an eyeball estimation portion detecting, based on the plurality of captured images, a position of an eyeball of the monitored subject and estimating a viewing area of the monitored subject based on the position of the eyeball; and
an estimation correction portion correcting a setup value, which is used by the direction estimation portion for estimating the viewing area based on the viewing area detected by the eyeball estimation portion.

7. The viewing area estimation device according to claim 6, further comprising:
a selection portion setting the viewing area estimated based on the position of the eyeball as a final viewing area when the eyeball estimation portion successfully estimates the position of the eyeball, and the selection portion setting the viewing area estimated by the direction estimation portion as the final viewing area when the eyeball estimation portion fails to estimate the position of the eyeball.

* * * * *